United States Patent [19]

Kaufman

[11] Patent Number: 4,585,443
[45] Date of Patent: Apr. 29, 1986

[54] CATHETER LOCATING DEVICE

[75] Inventor: Jerry M. Kaufman, Englishtown, N.J.

[73] Assignee: Hemedix International, Inc., Cambridge, Mass.

[21] Appl. No.: 544,249

[22] Filed: Oct. 21, 1983

[51] Int. Cl.[4] .............................................. A61M 5/32
[52] U.S. Cl. ................................... 604/174; 604/179; 128/DIG. 26
[58] Field of Search ............... 604/174, 175, 177, 178, 604/179, 180; 128/335, DIG. 26, 207.18, 207.17; 24/16 R, 459, 20 R, 20 EE

[56] References Cited

U.S. PATENT DOCUMENTS

| | | | |
|---|---|---|---|
| 2,008,340 | 7/1935 | Salvati et al. | 604/174 |
| 2,402,306 | 6/1946 | Turkel | 604/174 |
| 2,409,432 | 10/1946 | Hubbard | 604/179 |
| 4,198,989 | 4/1980 | Hawke et al. | 128/DIG. 26 |
| 4,316,461 | 2/1982 | Marais et al. | 604/179 |
| 4,392,857 | 7/1983 | Beran | 128/DIG. 26 |
| 4,445,893 | 5/1984 | Bodicky | 604/177 |
| 4,453,933 | 6/1984 | Speaker | 604/179 |

FOREIGN PATENT DOCUMENTS 488991 12/1952 Canada .............................. 604/179

Primary Examiner—C. Fred Rosenbaum
Assistant Examiner—Mario Costantino
Attorney, Agent, or Firm—Lerner, David, Littenberg, Krumlolz & Mentlik

[57] ABSTRACT

A device for securing catheters to grafts and the like implanted in patients, primarily for use in connection with dialysis treatments is disclosed, including an anchoring bracelet for attachment to the patient at a predetermined location at which the graft is located, and an adjustable saddle adjustably mounted on the anchoring bracelet, in which the saddle includes an aperture adapted to receive the catheter, a contact surface having a shape adapted to mate with the graft, and a saddle channel extending between the aperture and the contact surface, so that the catheter projects a predetermined distance from the contact surface when it has been inserted into the aperture, thereby permitting the catheter to be accurately located in the graft and firmly anchored on the patient. Such catheter devices including a catheter with a needle portion and a tubular catheter conduit for delivery of or removal of body fluids to the catheter is also disclosed.

32 Claims, 17 Drawing Figures

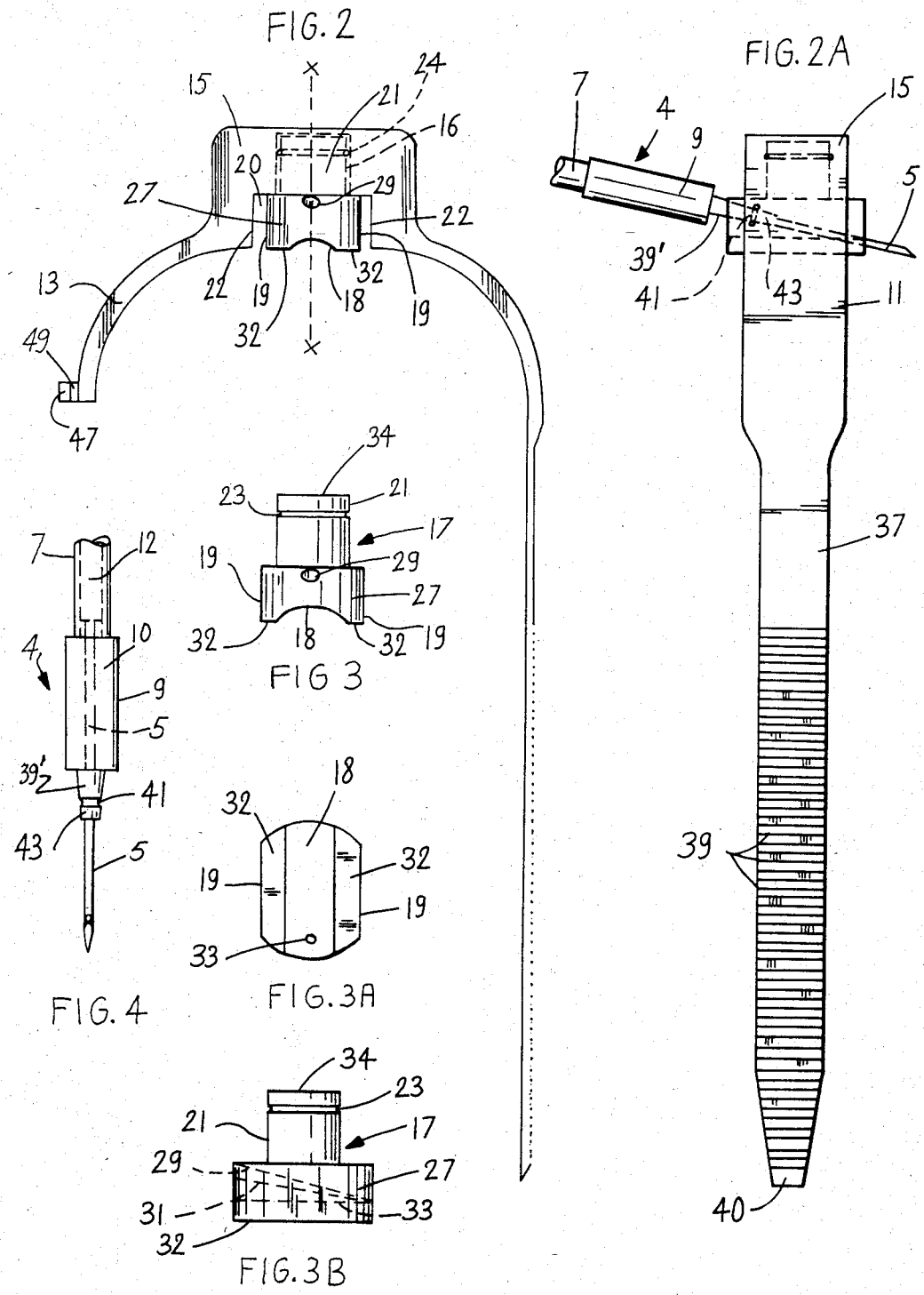

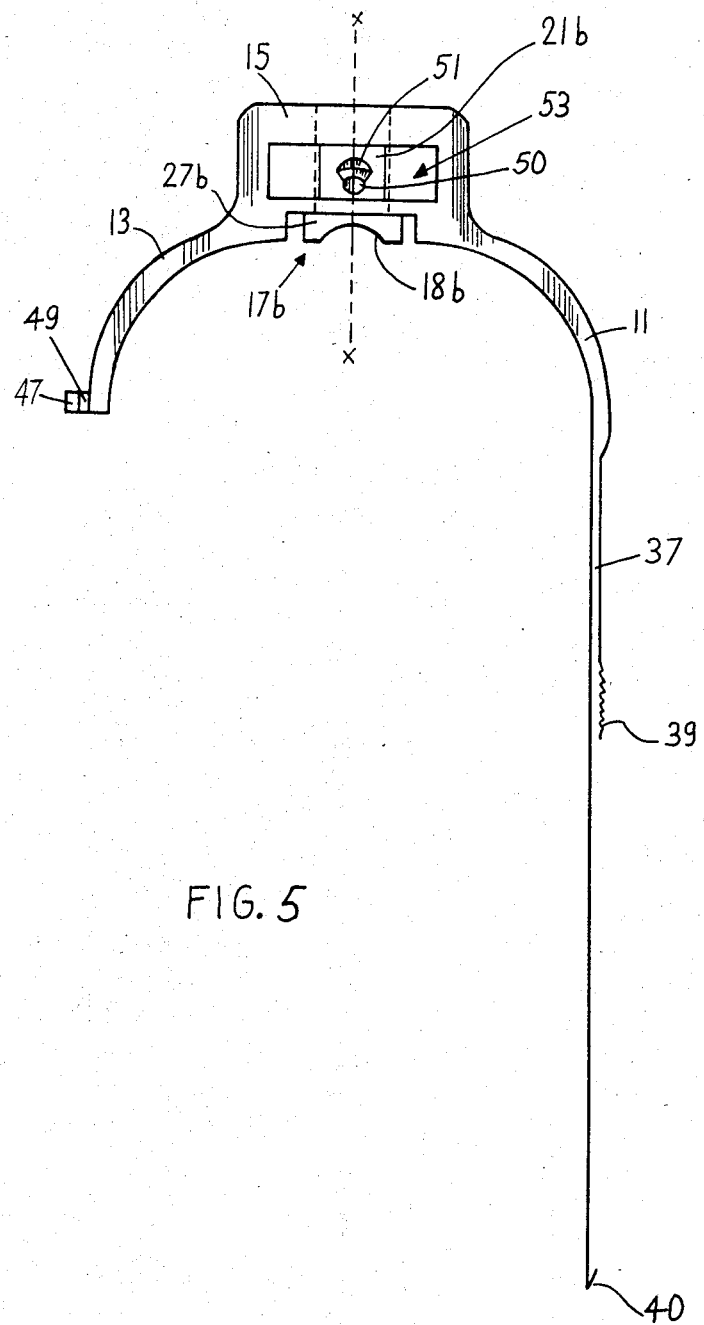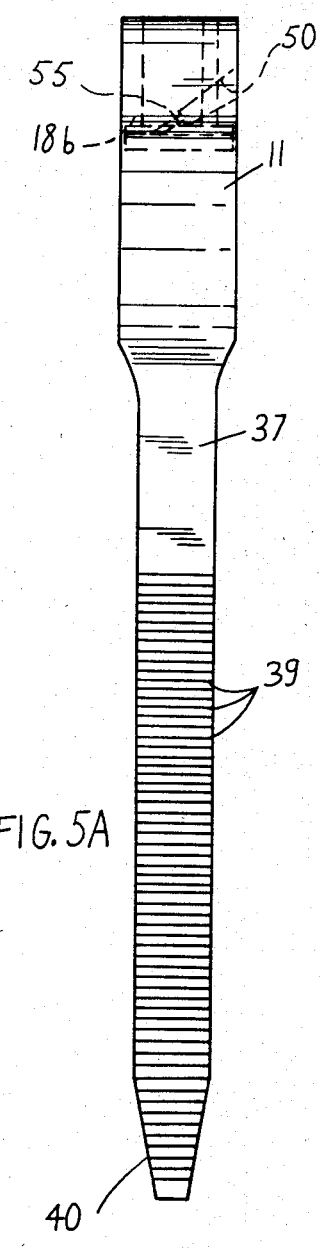

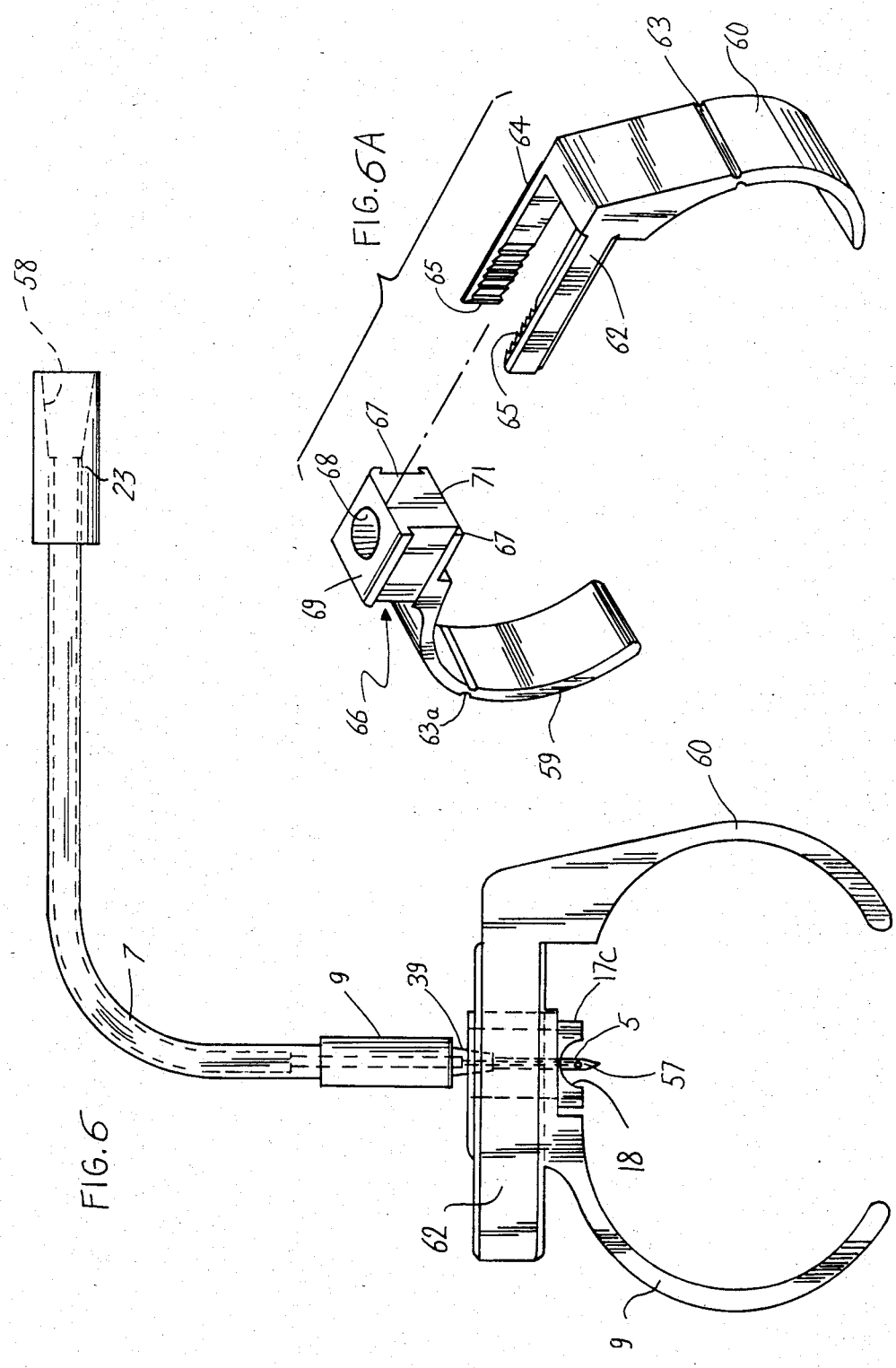

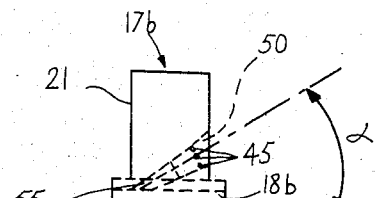
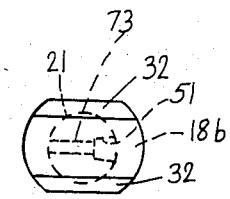
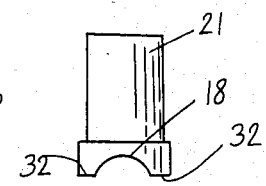
FIG. 7          FIG. 7A          FIG. 7B
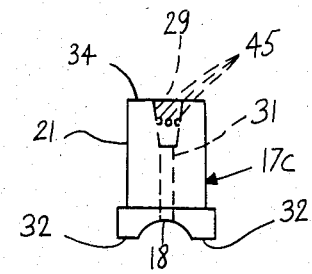
FIG. 7C
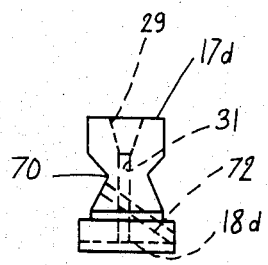
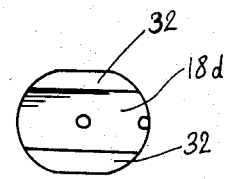
FIG. 7D          FIG. 7E

CATHETER LOCATING DEVICE

FIELD OF THE INVENTION

The present invention is directed to devices for securing catheters to patients. More particularly, the present invention is directed to devices for securing catheters within body fluid-carrying conduits, such as pre-implanted grafts, and particularly those used in connection with dialysis treatments. Still more particularly the present invention is directed to devices for firmly and accurately securing catheters to such body grafts so as to facilitate the constant dialysis techniques required for such patients.

BACKGROUND OF THE INVENTION

In the medical field the intravenous insertion of needles, catheters, cannulas and the like into a patient generally requires some means to secure the catheter or needle in place for the period of use. This has generally been done by positioning a gauze pad and/or by the application of strips of tape for securing the catheter and associated tubing to the patient so as to prevent any accidental removal of the catheter by sudden patient movement or the like. Obviously, the use of such a technique is not acceptable since the placement of the catheter is entirely non-uniform, or becomes a hit-or-miss proposition, proper placement of the catheter or needle is clearly not insured, such placement is quite slow, and is heavily dependent on the ability of the nurse or other technician who is applying the catheter, etc.

These problems become particularly acute in connection with the use of catheters in dialysis treatments, in which the patients generally require continual dialysis treatments and usually have a graft which has previously been implanted subcutaneously, and which requires continuing application and securing of the catheters during the entire dialysis procedure. Improper catheter application in such cases is thus not only painful, but this becomes a particularly harmful problem when the catheter misses or projects through the graft, thus invading the patient, with resultant problems of toxicity, etc. There has thus been a continuing search for new devices to replace the present ones and to insure proper application and securing of the catheter or needle.

In particular, one such device is shown in U.S. Pat. No. 2,402,306 to Turkel. The device in this patent includes a support for the needle with extending leaf members which can be attached by tape or the like. The support includes means for angular entry of the needle, and in the embodiment shown in FIGS. 4, 5, 9, and 10 thereof there is provision for altering the angle of the needle. However, as in the other prior art devices, it still becomes necessary to try to carefully aim the catheter into the desired injection site, and no physical means are provided for insuring that the catheter is properly placed and aligned with a pre-implanted graft or the like.

A number of prior art devices have also been developed which incorporate some type of attempt to mate with a vein or other body fluid-carrying conduit. These include U.S. Pat. No. 4,332,248 to DeVitis, which has a guide with a V-shaped lower surface for such purposes, as well as U.S. Pat. No. 4,316,461 to Marais et al and U.S. Pat. No. 4,059,105 to Cutruzzula et al.

A number of other such devices have also been employed in an attempt to maintain the catheters in place after angular insertion. These include U.S. Pat. No. 3,900,026 to Wagner, which includes a protective device for covering the catheter, U.S. Pat. No. 3,288,137 to Lund, and U.S. Pat. No. 3,021,842 to Flood.

The search has therefore continued for a practical device which can accurately and securely assist in fixing the catheter in place, i.e., not only by permitting insertion at precisely the right location, angle, and depth, but which can also firmly secure the catheter in place without additional difficulty.

SUMMARY OF THE INVENTION

In accordance with the present invention it has now been discovered that these and other objects can be realized by the utilization of a device for securing a catheter to a body fluid-carrying conduit in a patient which includes anchoring means for attachment to the patient at a predetermined location at which the body fluid-carrying conduit is located, and an adjustable saddle adjustably mounted on the anchoring means and including an aperture adapted to receive the catheter, a contact surface having a shape adapted to mate with the body fluid-carrying conduit in the patient, and a saddle channel extending between the aperture and the contact surface, so that the catheter projects a predetermined distance from the contact surface when it has been inserted into the aperture, thereby permitting the catheter to be accurately located in the body fluid-carrying conduit.

In one embodiment of the device of the present invention, the body fluid-carrying conduit is substantially cylindrical, and the contact surface of the adjustable saddle includes an arcuate portion for mating with that substantially cylindrical shape.

In a preferred embodiment of the device of the present invention, the adjustable saddle is rotatably mounted on the anchoring means so as to be at least partially rotatable about an axis substantially perpendicular to the contact surface.

In accordance with one embodiment of the device of the present invention the anchoring means includes a central portion and a pair of arm portions extending from opposite sides of the central portion, the arm portions being adapted to be affixed to the patient at the predetermined location. Preferably, the arm portions have an arcuate shape, and the device includes locking means for locking the anchoring means to the patient. Most preferably, these comprise one-way locking means.

In accordance with another embodiment of the device of the present invention, the body fluid-carrying conduit comprises a pre-implanted graft forming a portion of the circulatory system of the patient.

In accordance with a preferred embodiment of the device of the present invention, the locking means employed comprises a male locking member associated with one of the arm portions and a female locking member associated with the other arm portion. Preferably, the male locking member comprises an elongated strip member including a plurality of tooth members and the female locking member comprises a slot adapted to accept the elongated strip member, so that as the elongated strip member is inserted into the slot the plurality of tooth members sequentially lock with the slot so as to prevent removal of the elongated strip member from the slot.

In accordance with another embodiment of the device of the present invention, the central portion of the anchoring means includes first and second parallel surfaces, the male locking member comprises first and second track means associated with these first and second parallel surfaces, and the female locking member comprises first and second parallel arms extending from the arm portion with which the female locking member is associated, the first and second parallel arms being separated by a distance substantially corresponding to the distance between the first and second track means, whereby the first and second parallel arms can cooperate with the first and second track means in order to attach the central portion to the arm portion with which the female locking member is associated by inserting the first and second parallel arms into their corresponding first and second track means. In accordance with this embodiment, the preferred use of a plurality of tooth members on the first and second parallel arms permits these teeth to sequentially lock with the track means to prevent removal of the arms therefrom after they have been inserted into the corresponding track means.

In accordance with another embodiment of the device of the present invention, the aperture in the adjustable saddle includes stop means for limiting the depth to which the catheter may be inserted into the saddle channel. In a preferred embodiment, the stop means has a conical configuration which is adapted to mate with the shape of the catheter so as to stabilize the catheter after it has been inserted into the saddle channel.

In accordance with one embodiment of the device of the present invention, the saddle channel is disposed substantially parallel to the axis about which the saddle is rotatable. In another embodiment, however, the saddle channel may extend at an angle with respect to that axis.

In accordance with another embodiment of the device of the present invention, the aperture in the adjustable saddle comprises a first aperture, and the saddle channel is a first channel saddle, and the adjustable saddle includes a second aperture adapted to receive a catheter, and a second saddle channel extending between the second aperture and the contact surface, whereby the catheter may be inserted into either of the first or second apertures. In a preferred embodiment, the first saddle channel is disposed substantially parallel to the axis about which the saddle rotates, and the second saddle channel extends at an angle with respect to that axis.

In accordance with the catheter device of the present invention, there is provided a catheter including a needle member and tubular catheter conduit means for supplying fluid to or removing fluid from the needle member, anchoring means for attachment to the patient at a predetermined location at which a body fluid-carrying conduit is located, and an adjustable saddle adjustably mounted on the anchoring means, the adjustable saddle including an aperture adapted to receive the catheter, a contact surface having a shape adapted to mate with the body fluid-carrying conduit in the patient, and a saddle channel extending between the aperture and the contact surface, whereby the catheter projects a predetermined distance from the contact surface when it has been inserted into the aperture, thereby permitting the catheter to be accurately located in the body fluid-carrying conduit.

In accordance with one embodiment of the catheter device of the present invention, the aperture in the adjustable saddle includes stop means for limiting the depth to which the catheter may be inserted into the saddle channel. In a preferred embodiment, the tubular catheter conduit means and the aperture in the adjustable saddle have corresponding shapes intended to mate with each other so that the catheter is stabilized after it has been inserted into the saddle channel. In a preferred embodiment, the corresponding shapes comprise corresponding conical surfaces.

In a preferred embodiment of the catheter device of the present invention, the aperture in the adjustable saddle includes projecting means and the tubular catheter conduit means includes groove means at a location thereon corresponding to the location of the projecting means, so that when the catheter is inserted into the saddle channel the projecting means enter the groove means thereby locking the catheter into the saddle channel and preventing inadvertent removal thereof. In a preferred embodiment, the projecting means include a plurality of projecting members located circumferentially around the aperture.

In another embodiment of the catheter device of the present invention, the needle member includes a needle aperture so that the body fluid can flow through that needle aperture when the needle member is inserted into the body fluid-carrying conduit.

In a preferred embodiment of the catheter device of the present invention, the aperture in the adjustable saddle includes stop means for limiting the depth to which the catheter is inserted into the saddle channel, and preferably the stop means has a conical configuration and the tubular catheter conduit means includes a conical end portion, with these corresponding conical surfaces being adapted to mate with each other.

In another embodiment of the catheter device of the present invention, the adjustable saddle channel includes first and second apertures and corresponding first and second saddle channels extending between these apertures and the contact surface, with the catheter being disposed in one of these first and second apertures.

BRIEF DESCRIPTION OF THE DRAWINGS

The present invention may be more fully appreciated by referring to the drawings, wherein:

FIG. 2 is a side, elevational, perspective view of a device in accordance with the present invention in conjunction with a catheter;

FIG. 2A is a side, elevational, perspective view of the device shown in FIG. 2;

FIG. 3 is a side, elevational, perspective view of an adjustable saddle for use in connection with the device of the present invention;

FIG. 3A is a bottom, elevational, perspective view of the adjustable saddle shown in FIG. 3;

FIG. 3B is a front, elevational, perspective view of the adjustable saddle shown in FIG. 3;

FIG. 4 is a front, elevational, respective view of a catheter for use in connection with the device of the present invention;

FIG. 5 is a side, elevational, perspective view of another embodiment of the device of the present invention;

FIG. 5A is a side, elevational perspective view of the device shown in FIG. 5;

FIG. 6 is a side, elevational, perspective view of another embodiment of the device of the present invention in conjunction with a catheter;

FIG. 6A is a side, elevational, exploded view of the device shown in FIG. 6;

FIG. 7 is a side, elevational, perspective view of another adjustable saddle for use in connection with the device of the present invention;

FIG. 7A is a bottom, elevational, perspective view of the adjustable saddle shown in FIG. 7;

FIG. 7B is a front, elevational, perspective view of the adjustable saddle shown in FIG. 7;

FIG. 7C is a front, elevational, perspective view of the adjustable saddle shown in FIGS. 1 and 6;

FIG. 7D is a side, elevational, perspective view of another adjustable saddle for use in connection with the device of the present invention; and FIG. 7E is a bottom, elevational, perspective view of the adjustable saddle shown in FIG. 7D.

DETAILED DESCRIPTION

Figure 1:
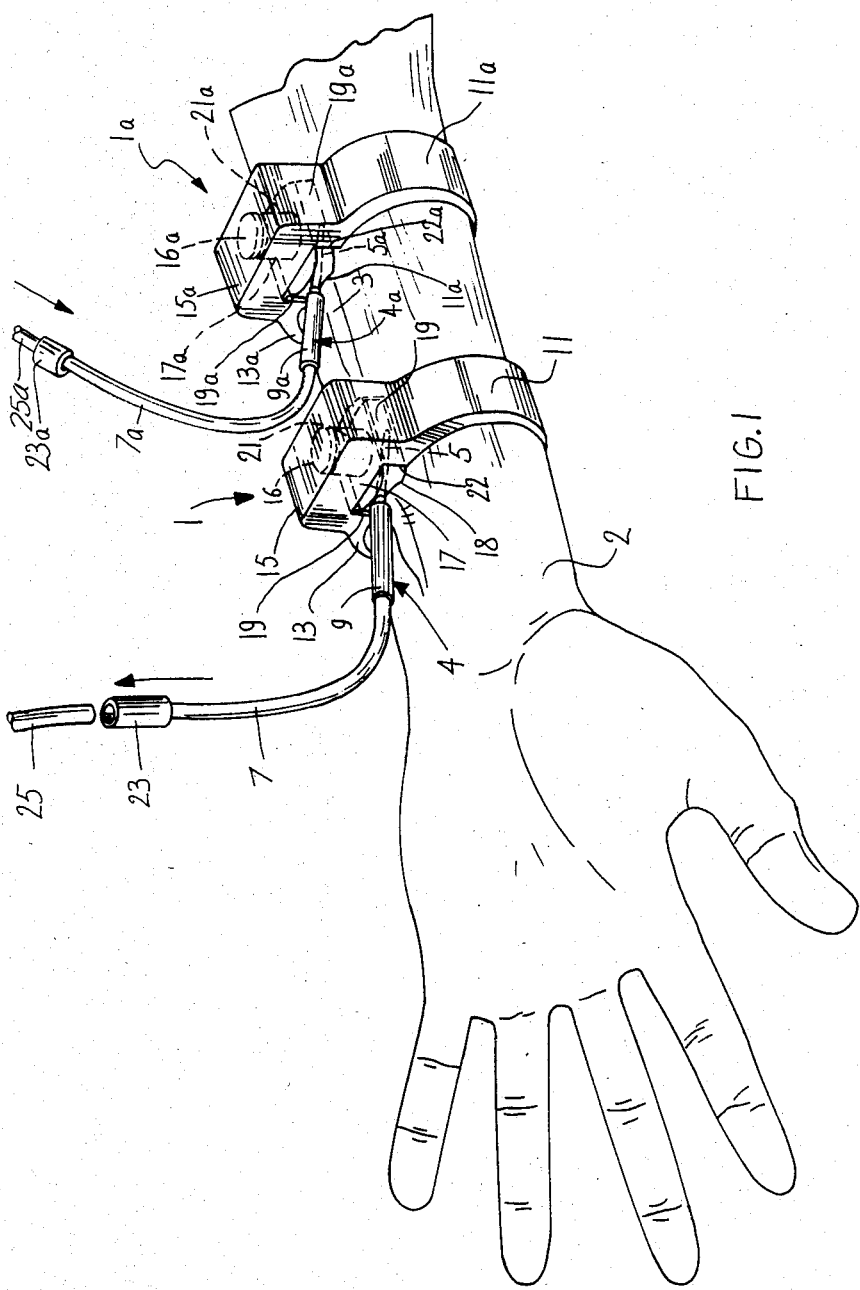
FIG. 1 is a top, elevational, perspective view of two devices in accordance with the present invention affixed to a patient.

The overall nature of the present invention can be more fully appreciated and understood with reference to the following detailed description thereof, which refers to the drawings herein, and in which like numerals refer to like portions thereof.

It is initially noted, however, that while the following discussion is specifically directed to the use of the device of the present invention in connection with a catheter for use with dialysis equipment, that the overall nature of the present invention is not limited to that specific mode of utilization. It will thus be appreciated by those of ordinary skill in this art that the illustrative discussion which follows, and which relates to use in dialysis, is not so limiting, and that the overall nature of the present invention makes it adaptable for other such uses in connection with the necessary placement and stabilization of catheters, needles, cannulas and the like.

Referring specifically to FIG. 1, a pair of the devices or "bracelets" of the present invention are shown as they would be used in connection with dialysis treatment of a patient. In particular, in this case the patient's arm 2 includes a previously imbedded graft 3 which has been subcutaneously applied to the dialysis patient's circulatory system in a previous surgical procedure. During dialysis treatment it is necessary to apply two catheters, a first catheter for removal of the impure blood from the patient and for the feeding of that impure blood to the dialysis equipment (not shown), and a second catheter for return of the then-purified blood back from the dialysis unit or equipment to the patient. In the case of FIG. 1, the first such device is the one designated 1, and the second such device, which accepts blood returned from the dialysis unit for entry back into the patient's circulatory system, is the device designated 1a, and is the device which is further up the patient's arm. The first device 1 can be referred to as the arterial device and the second or return device 1a can be referred to as the venus device.

In any event, the two devices 1 and 1a are shown in operable condition, with the catheters properly inserted into the graft 3. In this regard, the reference numerals followed by "a" are employed to designate portions of device 1a which correspond to the same portions of device 1, and the discussion which follows can thus relate to either such device. In each case, the catheters 4, 4a shown projecting into the graft 3, are thus secured and mounted on the devices 1 and 1a, respectively. The catheters 4, 4a include extending needle portions 5, 5a which are affixed to tubular conduits 7, 7a by means of plastic members 9, 9a. Insertion of the catheter into the bracelet device will be discussed in more detail below, but suffice it to say at this point that in FIG. 1 the devices are shown subsequent to such insertion.

In addition, each of the small lengths of tubular conduit 7, 7a is then available for connection to longer lengths of tubing 25, 25a by means of cylindrical connectors 23, 23a. Again, all of this is irrespective of the direction of blood flow in the device itself.

It is further noted that both of the catheters shown in FIG. 1 are disposed angularly with respect to the graft 3. In particular, they are shown at an acute or slight angle with respect thereto. This is a preferred embodiment of this invention. It has thus been realized that this form of catheter insertion is superior to, for example, a perpendicular needle insertion. In that latter case, the needle itself tends to oppose the flow of blood, causing undue pressure or blood disturbances. By using the device hereof, however, at the preferred angles, the needle does not oppose the blood flow and such disturbances are not created. In a particularly preferred embodiment an optimum angular placement of between about 10° and 15°, and most preferably about 12° is employed.

The devices 1 and 1a, which can be more clearly seen in FIGS. 2 and 2A, each includes a raised central portion 15, 15a as well as two extending arms 11, 11a and 13, 13a which have a radius of curvature which, in this case, is intended to closely match the radius of curvature of the patients arm 2 to which it will be affixed. Thus, for application to various other parts of the body, different such radii of curvature could be utilized, but the basic principle underlying such use would be the same.

Within the raised central portions 15, 15a, there are provided central aperture 16, 16a. Within these apertures 16, 16a are located adjustable or rotatable saddles 17, 17a, which can best be seen in FIGS. 3 through 3B. The saddles 17, 17a are preferably separate elements which can be inserted into the apertures 16, 16a, in the raised central portions 15, 15a of the devices 1, 1a. The saddles 17, 17a, include an upper cylindrical portion 21, 21a and a lower, elongated portion 27, 27a, including parallel sidewalls 19, 19a. Thus, it is the upper, cylindrical portion 21, 21a which is inserted into the corresponding cylindrical aperture 16, 16a in order to incorporate the saddle 17, 17a into the device 1, 1a itself. As shown in FIGS. 1 and 2, the raised central portion 15, 15a includes a lower, substantially rectangular opening 20, 20a defined by sidewalls 22, 22a. Thus, when the upper, cylindrical portion 21, 21a of the saddles 17, 17a has been inserted into the cylindrical aperture 16, 16a in the raised central portion 15, 15a, the lower, elongated portion 27, 27a of the saddle 17, 17a is now contained within lower, substantially rectangular opening 20, 20a. However, because of the clearance between the sidewalls 19, 19a of the lower, elongated portion 27, 27a of saddle member 17, 17a and the inner sidewalls 22, 22a of the cylindrical aperture 16, 16a in the raised central portions 15, 15a of the device, a substantial degree of rotation around axis X (as shown in FIG. 2) can now be achieved for the saddles 17, 17a. In fact, in a preferred embodiment the clearance between sidewalls 19, 19a and sidewalls 21, 21a will be sufficient to permit the saddles 17, 17a to rotate 360° about axis X. This permits the precise alignment and accurate placement of the catheter device hereof. In particular, when the device has thus been applied to the patient, as shown in FIG. 1, the axis X will be substantially perpendicular to the patient's skin. Thus, even after application of the device to the patient, but prior to insertion of the catheter itself, further fine alignment between the rotatable saddle 17, 17a and the graft 3 can be effected by rotation of the saddle 17, 17a about axis X, even by a small degree. This is again facilitated by the corresponding tubular shapes of the upper cylindrical portion 21, 21a of the saddles 17, 17a and of the internal surface of the opening 16, 16a in the raised central portion 15, 15a.

Mating of the saddle 17, 17a with the graft 3 is accomplished between the generally cylindrical shape of the graft 3 carrying blood therein, and the corresponding arcuate lower surface 18, 18a extending longitudinally along the bottom surface of the rotatable saddle 17, 17a.

The upper, cylindrical portion 21, 21a of the saddles 17, 17a have an upper surface 34, and a lower, elongated portion 27, 27a, which includes a longitudinally extending arcuate portion 18, 18a in the lower surface 32 of the lower, elongated portion 27, 27a. Upper, cylindrical portion 21, 21a also includes a circumferential groove 23 therein. This groove 23 is intended to mate with corresponding projections 23 within the cylindrical aperture 16, 16a. In this manner, when the saddle 17 is inserted into cylindrical aperture 16, the projections 24 will "snap" into the groove 23 when the saddle is at the proper location, so as to prevent any subsequent accidental removal of the saddle 17 thereafter. The projections 24 may be a series of projecting knobs, or possibly a continuous projection which will similarly enter the groove 23.

The lower, elongated portion 27 of the saddle 17 includes an aperture 29 at a central location thereon, as can best be seen in FIG. 3. This aperture 29 extends into a saddle channel 31 (see FIG. 3B) extending through the lower, elongated portion 27 of the saddle 17. Saddle channel 31 then terminates in an opening 33 in the arcuate portion 18 of the lower surface 32 (see FIG. 3A). In this manner, the catheter needle 5 can be inserted into the aperture 29, and thus into the saddle channel 31, so that the tip of the needle 5 ultimately extends through opening 33 by a predetermined distance, as can best be seen in FIGS. 2A and 6. That predetermined distance is such that the tip of the needle 5 will then be located substantially in the center of the graft 3 after insertion of the catheter. The correct amount of such penetration and stabilization of the catheter is further determined by the relationship between aperture 29 and the catheter 4 itself. As can best be seen in FIG. 2, the catheter 4 includes connector 9 for connecting the tubular conduit 7 to the needle 5. The connector 9 is preferably prepared from a relatively rigid material, such as plastic, and includes a central, cylindrical portion 10, and an extending portion 12 which has a reduced diameter. In this manner, the conduit 7, which is composed of rubber, having a much less rigid structure than connector 9, can be sealably affixed to the connector 9 by being slid over the extending portion 12 in the manner shown. A small amount of epoxy or other such adhesive can be applied to the outer surface of extending portion 12 prior to application of the conduit 7 if desired, in order to solidify the bond therebetween. The other end of the cylindrical portion 10 includes tapered portion 39, which terminates at an end portion 43 which includes an aperture for snuggly fitting about the needle 5 inserted therein. The conical or tapered shape of the tapered portion 39 is adapted to mate with the corresponding conical or tapered shape of the aperture 29 in the saddle 17, as can be seen in FIG. 2A, for firmly holding the catheter 4 in its desired position and depth, and for preventing premature removal or undesired movement thereof. Furthermore, a plurality of projections 45 are circumferentially disposed in a circular array within aperture 29, while at a corresponding location on the tapered portion 39 of the connector 9 a groove 41 is included for the purpose of locking the catheter 4 in place so that it cannot be inadvertently removed from aperture 29. Thus, upon insertion of the catheter 4 into the saddle 17 to the desired depth, the projections 45 will enter groove 41 and lock the catheter 4 into position therein.

The following discussion concerns application of the bracelet device itself to the patient's arm 2, or to some other portion of the patient's anatomy. In the embodiment shown in FIGS. 2 and 2A securing and locking of the device of this invention is facilitated by means of an elongated strip 37 extending from arm 11 and including on at least a portion of its outer surface a plurality of teeth 39 as shown. These teeth act in the manner of a ratchet, and cooperate with slot 49 which is located on the arm 13 projecting from the other side of raised central portion 15. Thus, by insertion of the distal end 40 of the strip 37 into slot 49 defined by U-shaped member 47, as each of the teeth 39 passes through slot 49 the device is sequentially locked onto the patient's arm to which it has been applied, since each such tooth cannot now pass back through slot 49 in view of its saw-toothed shape, also shown in FIG. 2. The amount by which the strip 37 is passed through slot 49 will, of course, depend upon the size of the patient's arm, etc.

Another embodiment of the device of this invention which is similar in this respect is shown in FIGS. 5 and 5A. However, in this embodiment the rotatable saddle 17 has been replaced with rotatable saddle 17b, which has a slightly different configuration. In this embodiment, the saddle 17b has generally the same configuration as saddle 17, but in this case the upper, cylindrical portion 21b is relatively longer, while the lower, elongated portion 27b is flatter than the corresponding portion 27 of the saddle 17. Furthermore, the rotatable saddle 17b includes an aperture 50 located in its upper, cylindrical portion 21b, and this aperture 50 then extends into a saddle channel 55, which in turn opens into the arcuate portion 18b in the lower face of the lower elongated portion 27b. Furthermore, in connection with this embodiment, the central raised portion 15 of the bracelet device includes a rectangular slot or window 53 in its side portion, through which the catheter 4 can be inserted. The catheter 4 can now be inserted through window 53 into aperture 50 and channel 55, and thus affixed thereto in much the same manner as was the case in connection with the embodiment shown in FIGS. 1-4.

Yet another embodiment of the device hereof is shown in FIGS. 6 and 6A hereof. In this embodiment the device is divided into two separate but interconnectable sections, as can best be seen in FIG. 6A. This device thus still includes a central raised portion 69 and two arcuate arm portions 59 and 60. However, arm portions 59 and 60 are now separate, with arcuate arm portion 59 being affixed to the central raised portion 69 and arcuate arm portion 60 being separate therefrom. The two portions can thus be connected, and at the same time the device can be affixed to the patient's arm by means of cooperation between a pair of parallel track portions 67 on either side of raised portion 69, and a pair of corresponding arms 62 and 64 extending from the arcuate arm portion 60. These extending arm portions 62 and 64 include on their inner surface a plurality of teeth 65, again acting as a ratchet member, so that when the two portions of the device are brought together in the manner shown in FIG. 6, extending arms 62 and 64 are separated by a sufficient distance so as to enter tracks 67, and by the cooperation of the teeth 65 with the end of tracks 67, a one-way lock is again formed, and for much the same purposes as was discussed above with regard to the embodiment shown in FIG. 5, as well as for the purpose of joining the two halves of the device together. As in the other embodiments of this invention, the central raised portion 69 again includes aperture 68 corresponding to the apertures discussed above in this case for placement of the rotatable saddle 17c. Upon insertion of the catheter 4 in the manner shown in FIG. 5, the needle portion 5 of the catheter 4 will again extend to the predetermined depth below the arcuate portion 18, and thus into the graft 3. It can also be seen in FIG. 6 that the needle portion 5 of the catheter includes an opening 57 in proximity to the tip of needle 5 so that flow of blood through the portion of the needle within the graft 3 is facilitated. It is also noted that in this embodiment, the catheter 4 is inserted perpendicularly into the graft 3. However, this is a far less preferred embodiment than the angular insertions discussed above. The device shown in FIGS. 6 and 6A can be altered slightly so as to also operate with such angular insertion, such as by relocating the aperture 68 from the upper surface of raised portion 69 into the sidewall 66 thereof, for example. Of course, the corresponding saddle channels would have to be similarly relocated.

Finally, in FIGS. 7–7E various embodiments of the rotatable saddle 17 are shown. The embodiment shown in FIGS. 7–7B sets forth in greater detail the rotatable saddle 17b discussed in connection with FIGS. 5 and 5A. In FIG. 7C there is shown a rotatable saddle 17c, which in this case again corresponds to rotatable saddle 17, but now includes a perpendicular saddle channel 31 connected to aperture 29, which is now located on the upper surface 34 of the upper, cylindrical portion 21 of the saddle 17c. Similarly, the saddle channel 31 in this case will now open into the central portion of the arcuate portion 18 of the lower surface 32. Of course, in such an embodiment it would also be necessary to alter the configuration of the raised central portion 15 of the bracelet itself. It will thus require an opening in its upper surface in order to accommodate entry of the catheter 4 into the upper surface 34 of the saddle 17c. In any event, and as is discussed above, this embodiment is far less preferred precisely because it results in perpendicular insertion of the catheter 4, as compared to the angular insertion achieved in connection with the embodiments set forth above. In the embodiment shown in FIGS. 7D and 7E, two such saddle channels 31 and 72 are shown. In this case, two apertures 29 and 70 are shown, including corresponding saddle channels 31 and 72, respectively. In this manner, the channels 31 and 72 both open into the arcuate portion 18d, as can best be seen in FIG. 7E, and the catheter 4 can be inserted either perpendicularly or angularly, as desired, depending upon which channel is selected. Of course, the bracelet itself to be used in connection with this embodiment will need to accommodate both such potential catheters.

It is also noted that in the embodiment shown in FIG. 6A frangible portions 63 and 63a are shown on each of the arcuate arm portions 60 and 59, respectively. These frangible portions 63, 63a, which are essentially areas of substantially reduced thicknesses, are designed to permit removal of the entire bracelet device of this invention after use, by merely fracturing the bracelet at frangible portions 63 and 63a, i.e., by bending the arm portions outwardly. This embodiment can be incorporated into other embodiments of the devices of the present invention.

It will be understood that the embodiment described herein is merely exemplary and that a person skilled in the art may make many variations and modifications without departing from the spirit and scope of the invention. All such modifications and variations are intended to be included within the scope of the invention as defined in the appended claims.

I claim:

1. A device for securing a catheter to a body fluid-carrying conduit in a patient comprising anchoring means for attachment to said patient at a predetermined location at which said body fluid-carrying conduit is located, and an adjustable saddle rotatably mounted on said anchoring means, said adjustable saddle including an apeture adapted to receive said catheter, and a contact surface adapted for alignment with said body fluid-carrying conduit in said patient, and a saddle channel extending between said aperture and said contact surface, said adjustable saddle being at least partially rotatable about an axis substantially perpendicular to said contact surface, whereby said adjustable saddle may be rotated after said device has been attached to said patient, so as to permit said catheter to be accurately located in said body fluid-carrying conduit upon its insertion into said aperture.

2. The device of claim 1, wherein said body fluid-carrying conduit is substantially cylindrical and said contact surface of said adjustable saddle includes an arcuate portion for mating with said substantially cylindrical shape of said body fluid-carrying conduit.

3. The device of claim 1, wherein said anchoring means comprises a central portion and a pair of arm portions extending from opposite sides of said central portion, said arm portions being adapted to be affixed to said patient at said predetermined location.

4. The device of claim 3, wherein said arm portions are arcuate in shape.

5. The device of claim 3, including locking means for locking said anchoring means to said patient.

6. The device of claim 5, wherein said locking means comprises one-way locking means.

7. The device of claim 5, wherein said locking means comprises a male locking member associated with one of said arm portions and a female locking member associated with the other of said arm portions.

8. The device of claim 7, wherein said male locking member comprises an elongated strip member including a plurality of tooth members and said female locking member comprises a slot adapted to accept said elongated strip member, whereby as said elongated strip member is inserted into the slot said plurality of tooth members sequentially lock with said slot so as to prevent removal of said elongated strip member from said slot.

9. The device of claim 7, wherein said central portion of said anchoring means includes first and second parallel surfaces, said male locking member comprises first and second track means associated with said first and second surfaces, and said female locking member comprises first and second parallel arms extending from said arm portion with which said female locking member is associated, said first and second parallel arms being separated by a distance substantially corresponding to the distance between said first and second track means of said central portion of said anchoring means, whereby said first and second parallel arms can cooperate with said first and second track means to attach said central portion to said arm portion with which said female locking member is associated by inserting said first and second parallel arms into said corresponding first and second track means.

10. The device of claim 9 wherein said first and second parallel arms each include a plurality of tooth members whereby as said first and second parallel arms are inserted into said corresponding first and second track means said plurality of tooth members sequentially lock with said track means so as to prevent removal of said first and second parallel arms from said track means.

11. The device of claim 1 wherein said anchoring means includes a central aperture, and said adjustable saddle is mounted in said central aperature.

12. The device of claim 1 wherein said aperture in said adjustable saddle includes stop means for limiting the depth to which said catheter may be inserted into said saddle channel.

13. The device of claim 12 wherein said stop means has a conical configuration adapted to mate with the shape of said catheter so as to stabilize said catheter after it has been inserted into said saddle channel.

14. The device of claim 1, wherein said saddle channel is substantially parallel to said axis.

15. The device of claim 1, wherein said saddle channel extends at an angle with respect to said axis.

16. The device of claim 1, wherein said aperture in said adjustable saddle comprises a first aperture, and said saddle channel comprises a first saddle channel, and including a second aperture in said adjustable saddle adapted to receive a catheter, and a second saddle channel extending between said second aperture and said contact surface, whereby said catheter may be inserted into either of said first or second apertures.

17. The device of claim 16, wherein said first saddle channel is substantially parallel to said axis and said second saddle channel extends at an angle with respect to said axis.

18. A catheter device for being affixed to a body fluid-carrying conduit in a patient comprising a catheter including a needle member and a tubular catheter conduit means for supplying fluid to or removing fluid from said needle member, anchoring means for attachment to said patient at a predetermined location at which said body fluid-carrying conduit is located, and an adjustable saddle rotatably mounted on said anchoring means, said adjustable saddle including an aperture adapted to receive said catheter, and a contact surface adapted for alignment with said body fluid-carrying conduit in said patient, and a saddle channel extending between said aperture and said contact surface, said adjustable saddle being at least partially rotatable about an axis substantially perpendicular to said contact surface, whereby said catheter is accurately located in said body fluid-carrying conduit upon its insertion into said aperture.

19. The catheter device of claim 18, wherein said body fluid-carrying conduit is substantially cylindrical and said contact surface of said adjustable saddle includes an arcuate portion for mating with said substantially cylindrical shape of said body fluid-carrying conduit.

20. The catheter device of claim 18, wherein said aperture in said adjustable saddle includes stop means for limiting the depth to which said catheter may be inserted into said saddle channel.

21. The catheter device of claim 20 wherein said tubular catheter conduit means and said aperture in said adjustable saddle have corresponding shapes whereby said catheter is stabilized after it has been inserted into said saddle channel.

22. The catheter device of claim 21, wherein said corresponding shapes of said tubular catheter conduit means and said aperture in said adjustable saddle comprise corresponding conical surfaces.

23. The catheter device of claim 21, wherein said aperture in said adjustable saddle includes projecting means and said tubular catheter conduit means comprises groove means at a location thereon corresponding to the location of said projecting means, whereby said catheter is locked in said aperture after said catheter has been inserted into said saddle channel.

24. The catheter device of claim 23, wherein said projecting means includes a plurality of projecting members located circumferentially around said aperture in said adjustable saddle.

25. The catheter device of claim 18 wherein said needle member includes a needle aperture whereby said body fluid can flow through said needle aperture when said needle member is inserted into said body fluid-carrying conduit.

26. The catheter device of claim 18, wherein said anchoring means comprises a central portion and a pair of arm portions extending from opposite sides of said central portion, said arm portions being adapted to be affixed to said patient at said predetermined location.

27. The catheter device of claim 26, wherein said arm portions are arcuate in shape.

28. The catheter device of claim 26, including locking means for locking said anchoring means to said patient, said locking means comprising a male locking member associated with one of said arm portions and a female locking member associated with the other of said arm portions.

29. The catheter device of claim 18, wherein said anchoring means includes a central aperture, and said adjustable saddle is mounted in said central aperture.

30. The catheter device of claim 18, wherein said aperture in said adjustable saddle includes stop means for limiting the depth to which said catheter is inserted into said saddle channel.

31. The catheter device of claim 20, wherein said stop means has a conical configuration, and said tubular catheter conduit means includes a conical end portion, said conical surfaces being adapted to mate with each other.

32. The catheter device of claim 18, wherein said aperture in said adjustable saddle comprises a first aperture, and said saddle channel comprises a first saddle channel, and including a second aperture in said adjustable saddle adapted to receive said catheter, and a second saddle channel extending between said second aperture and said contact surface, said catheter being disposed in one of said first and second apertures.

* * * * *

UNITED STATES PATENT AND TRADEMARK OFFICE
CERTIFICATE OF CORRECTION

PATENT NO. : 4,585,443

DATED : April 29, 1986

INVENTOR(S) : Jerry M. Kaufman

It is certified that error appears in the above-identified patent and that said Letters Patent is hereby corrected as shown below:

```
Column 6, line 15, "ia" should read --is--.
Column 12, line 54, "20" should read --30--.
```

Signed and Sealed this

Twenty-sixth Day of August 1986

[SEAL]

Attest:

DONALD J. QUIGG

Attesting Officer

Commissioner of Patents and Trademarks